(12) United States Patent
Min et al.

(10) Patent No.: US 11,484,705 B2
(45) Date of Patent: *Nov. 1, 2022

(54) IMPLANTABLE MEDICAL SYSTEMS AND METHODS INCLUDING PULSE GENERATORS AND LEADS

(71) Applicant: Pacesetter, Inc., Sylmar, CA (US)

(72) Inventors: Xiaoyi Min, Simi Valley, CA (US); Avi Fischer, New Rochelle, NY (US); Kyungmoo Ryu, Palmdale, CA (US); Gabriel A. Mouchawar, Valencia, CA (US)

(73) Assignee: Pacesetter, Inc., Sylmar, CA (US)

( * ) Notice: Subject to any disclaimer, the term of this patent is extended or adjusted under 35 U.S.C. 154(b) by 236 days.

This patent is subject to a terminal disclaimer.

(21) Appl. No.: 16/859,247

(22) Filed: Apr. 27, 2020

(65) Prior Publication Data

US 2020/0254238 A1    Aug. 13, 2020

Related U.S. Application Data

(63) Continuation of application No. 15/973,219, filed on May 7, 2018, now Pat. No. 10,722,704.

(51) Int. Cl.
*A61N 1/05* (2006.01)
*A61N 1/39* (2006.01)
*A61B 5/0245* (2006.01)

(52) U.S. Cl.
CPC .......... *A61N 1/0587* (2013.01); *A61B 5/0245* (2013.01); *A61N 1/0504* (2013.01); *A61N 1/3918* (2013.01); *A61N 1/3956* (2013.01); *A61N 1/3968* (2013.01); *A61N 1/3987* (2013.01)

(58) Field of Classification Search
CPC ........................... A61N 1/0587; A61N 1/0245
USPC .............................................................. 607/5
See application file for complete search history.

(56) References Cited

U.S. PATENT DOCUMENTS

| 6,866,044 B2 | 3/2005 | Bardy et al. |
| 7,149,575 B2 | 12/2006 | Ostroff et al. |
| 7,536,222 B2 | 5/2009 | Bardy et al. |
| 7,655,014 B2 | 2/2010 | Ko et al. |
| 7,774,059 B2 | 8/2010 | Ostroff et al. |
| 8,831,720 B2 | 9/2014 | Bardy et al. |

(Continued)

OTHER PUBLICATIONS

De Maria et al.; "The Entirely Subcutaneous Defibrillator (S-ICD): State of the Art and Selection of the Ideal Candidate" Current Cardiology Reviews; 2015; 7 pages.

(Continued)

*Primary Examiner* — Nadia A Mahmood (74) *Attorney, Agent, or Firm* — The Small Patent Law Group LLC; Dean D. Small (57) ABSTRACT

Methods for implanting a pulse generator (PG) within a pectoral region of a chest of a patient and devices having the PG. The PG has a housing that includes a PG electrode. Methods also include implanting at least one lead having first and second electrode segments with the first electrode segment positioned along an anterior of the chest of the patient and the second electrode segment positioned along at least one of a posterior of the patient or a side of the patient. The first and second electrode segments are positioned subcutaneously at or below an apex of a heart of the patient, wherein the PG electrode and the first and second electrode segments are configured to provide electrical shocks for antiarrhythmic therapy.

20 Claims, 5 Drawing Sheets

(56) References Cited

U.S. PATENT DOCUMENTS

| | | |
|---|---|---|
| 9,295,834 B2 | 3/2016 | Wulfman et al. |
| 2002/0049475 A1 | 4/2002 | Bardy et al. |
| 2016/0121130 A1 | 5/2016 | Cinbis et al. |

OTHER PUBLICATIONS

Kempa et al.; "Implantation of additional Subcutaneous Array Electrode Reduces Defibrillation Threshold in ICD Patients—Preliminary Results" Archives of Medical Science: AMS; 2012; 5 pages.

IMPLANTABLE MEDICAL SYSTEMS AND METHODS INCLUDING PULSE GENERATORS AND LEADS

REFERENCE TO RELATED APPLICATIONS

The present application is a continuation application of, and claims priority to, U.S. application Ser. No. 15/973,219, Titled "IMPLANTABLE MEDICAL SYSTEMS AND METHODS INCLUDING PULSE GENERATORS AND LEADS" which was filed on May 7, 2018, the complete subject matter of which is expressly incorporated herein by reference in its entirety.

BACKGROUND

Embodiments of the present disclosure relate generally to subcutaneous implantable medical devices and methods, and more particularly to medical devices having pulse generators and leads that are implanted subcutaneously.

Currently, implantable medical devices (IMD) are provided for a variety of cardiac applications. IMDs may include a "housing" or "canister" (or "can") and one or more electrically-conductive leads that connect to the canister through an electro-mechanical connection. IMDs may contain electronics (e.g., a power source, microprocessor, capacitors, etc.) that control electrical activation of the leads to provide various functionalities. For instance, the IMD may be configured for pacemaking, cardioversion, and/or defibrillation. An implantable cardioverter-defibrillator (ICD) is one such medical device and it is designed to monitor heart rate, recognize certain events (e.g., ventricular fibrillation or ventricular tachycardia), and deliver electrical shock to reduce the risk of sudden cardiac death (SCD) from these events. The ICD may be used for patients who have already experienced potentially life-threatening events or for those that are at risk of SCD. The ICD includes a pulse generator and one or more leads having electrodes that may be used to detect how the heart is functioning or provide electrical shock to the heart.

One type of ICD delivers therapy through transvenous leads that are advanced to the right ventricle for detection and treatment of tachyarrhythmia. Transvenous ICDs (or TV-ICDs) may also provide bradycardia-pacing support. Although TV-ICDs can be helpful and prevent sudden cardiac death, TV-ICDs may have certain drawbacks or potential complications. For instance, it can be difficult and time-consuming to achieve venous access, thereby prolonging the medical procedure. TV-ICDs can be associated with hemopericardium, hemothorax, pneumothorax, lead dislodgement, lead malfunction, device-related infection, and venous occlusion. Transvenous leads may also malfunction through conductor failure in the leads or breaches in the insulation that surrounds the conductors.

A second type of ICD, referred to as a subcutaneous ICD (or S-ICD), uses an electrode configuration that can reside entirely within the subcutaneous space. The pulse generator is positioned along a side of the patient's chest below the arm pit (e.g., over the sixth rib near the left mid-axillary line). A lead extends from the pulse generator along the side of the patient toward the sternum. The lead then turns to extend parallel to the mid-sternal line and is positioned adjacent to the sternum extending between the xiphoid process and the manubriosternal junction. This portion of the lead includes a shock coil that is flanked by two sensing electrodes. The sensing electrodes sense the cardiac rhythm and the shock coil delivers counter-shocks through the subcutaneous tissue of the chest wall. Unlike the transvenous types, the S-ICDs lack intravenous and intracardiac leads and, as such, are less likely to have the noted complications associated with more invasive devices. Current electrode configurations for S-ICDs, however, have some challenges or undesirable features. For instance, S-ICDs typically have a relatively large canister (e.g., about 70 cc) to provide a sufficient amount of energy for defibrillation.

Accordingly, a need remains for alternative S-ICD electrode configurations that provide a sufficient amount of energy for defibrillation.

SUMMARY

Embodiments set forth herein include implantable medical devices (SIMDs), systems that include SIMD, and methods of using and positioning the same. SIMDs may include a pulse generator and at least one lead. The at least one lead may have multiple segments. The segments may be separate or may be portions of a single elongated coil. In some embodiments, the entire SIMD may be positioned subcutaneously (e.g., beneath the skin but above layers of skeletal muscle tissue, rib bones, and costal cartilage). In some embodiments, only designated elements of the SIMD are positioned subcutaneously. In other embodiments, at least some elements of the SIMD may be positioned submuscularly. For example, the pulse generator may be implanted submuscularly (e.g., under the serratus anterior muscle) or under the serratus anterior fascia but above muscle.

In accordance with one or more embodiments herein, a method is provided that includes implanting a pulse generator (PG) within a pectoral region of a chest of a patient. The PG has a housing that includes a PG electrode. The method also includes implanting at least one lead having first and second electrode segments with the first electrode segment positioned along an anterior of the chest of the patient and the second electrode segment positioned along at least one of a posterior of the patient or a side of the patient. The first and second electrode segments are positioned subcutaneously at or below an apex of a heart of the patient, wherein the PG electrode and the first and second electrode segments are configured to provide electrical shocks for antiarrhythmic therapy.

In some aspects, the first and second electrode segments are portions of a common lead coil that extends from a proximal end of the first electrode segment to a distal end of the second electrode segment. The common lead coil extends along the chest of the patient from the anterior of the chest toward the side of the patient, wherein the second electrode segment extends to or beyond a midaxillary line of the patient.

In some aspects, an active length of the common lead coil is at least 35 cm from the proximal end of the first electrode segment to the distal end of the second electrode segment.

In some aspects, the first and second electrode segments are spaced apart from one another, the second electrode segment being longer than the first electrode segment. Optionally, the second electrode segment has an active length measured between proximal and distal ends of the second electrode segment. The active length is at least 12 centimeters (cm), wherein the second electrode segment extends beyond a posterior axillary line.

In some aspects, implanting the at least one lead includes positioning one lead such that the one lead extends away from the pulse generator, extra-thoracically along the sternum, and along an intercostal gap so that a distal end of the one lead is positioned at or beyond a midaxillary line of the patient.

In some aspects, implanting the first electrode segment includes tunneling from a pocket where the pulse generator is positioned along a sternum of the patient to an intercostal gap at or below the apex of the heart.

In some aspects, implanting the second electrode segment includes making a tunnel that extends along an intercostal gap between a first access incision proximate to the xiphoid process and a second access incision that is positioned at or beyond a midaxillary line.

In some aspects, implanting the pulse generator includes making a subcutaneous pocket and positioning the pulse generator within the subcutaneous pocket.

In some aspects, the first and second electrode segments are portions of a continuous elongated body that wraps about the patient, wherein implanting the first electrode segment and the second electrode segment includes making a xiphoid incision and an access incision at or beyond a midaxillary line near an intercostal gap.

In some aspects, the first electrode segment has an active length that extends between a proximal end and a distal end of the first electrode segment. The active length is between 5 and 12 cm.

In some aspects, a defibrillation threshold (DFT) is at most 50 Joules and a volume of the pulse generator is at most 40 milliliters.

In accordance with one or more embodiments herein, a subcutaneous implantable medical system is provided that includes a pulse generator (PG) configured to be positioned subcutaneously within a pectoral region of a chest of a patient. The PG has a housing that includes a PG electrode. The PG has an electronics module. The subcutaneous implantable medical system also includes an elongated lead that is electrically coupled to the pulse generator. The elongated lead includes a first electrode segment that is configured to be positioned along an anterior of the chest of the patient and a second electrode segment that is configured to be positioned along at least one of a posterior of the patient or a side of the patient. An active length of the lead body extends between a proximal end of the first electrode segment and a distal end of the second electrode segment. The active length is at least 35 centimeters (cm), wherein the electronics module is configured to provide electrical shocks for antiarrhythmic therapy using the PG electrode and the first and second electrode segments.

In some aspects, the first and second electrode segments are portions of a common lead coil that extends from a proximal end of the first electrode segment to a distal end of the second electrode segment. The lead coil is sized to extend along the chest of the patient from the anterior of the chest to the posterior of the patient. An active length of the common lead coil is at least 35 cm from the proximal end of the first electrode segment to the distal end of the second electrode segment.

In some aspects, the first and second electrode segments are spaced apart from one another. The second electrode segment is longer than the first electrode segment. The second electrode segment has an active length measured between proximal and distal ends of the second electrode segment. The active length is at least 12 cm, wherein the second electrode segment extends beyond a posterior axillary line.

In some aspects, the first electrode segment has an active length measured between proximal and distal ends of the first electrode segment. The active length is between 5 and 12 cm.

In some aspects, a defibrillation threshold (DFT) is at most 50 Joules and a volume of the PG is at most 40 milliliters.

In accordance with one or more embodiments herein, a method of treating a patient is provided. The method includes sensing cardiac activity of a patient with a subcutaneous implantable medical system. The subcutaneous implantable medical system includes a pulse generator (PG) positioned subcutaneously within a pectoral region of a chest of the patient. The subcutaneous implantable medical system also includes a first electrode segment positioned along an anterior of the chest of the patient and a second electrode segment positioned along at least one of a posterior of the patient or a side of the patient. The first and second electrode segments are positioned subcutaneously at or below an apex of a heart of the patient. The method also includes providing antiarrhythmic therapy, based on the cardiac activity, by providing electrical shocks or pulses between the first and second electrode segments and an electrode of the PG.

In some aspects, the first and second electrode segments are portions of a common lead coil that extends from a proximal end of the first electrode segment to a distal end of the second electrode segment. The lead coil extends along the chest of the patient from the anterior of the chest to the posterior of the patient. An active length of the common lead coil is at least 35 cm from the proximal end of the first electrode segment to the distal end of the second electrode segment.

In some aspects, the first and second electrode segments are spaced apart from one another. The second electrode segment is longer than the first electrode segment. The second electrode segment has a length that is at least 12 centimeters (cm), wherein a defibrillation threshold (DFT) is at most 50 Joules and a volume of the PG is at most 40 milliliters.

In accordance with one or more embodiments herein, a method is provided that includes implanting a pulse generator (PG) within a pectoral region of a chest of a patient. The PG has a housing that includes a PG electrode. The method also includes implanting at least one lead having a common lead coil that extends from a proximal end to a distal end. The proximal end position along an anterior of the chest of the patient, and the distal end positioned along at least one of a posterior or a side of the patient. The common lead coil is positioned subcutaneously. At least a majority of the common lead coil is positioned at or below an apex of a heart of the patient, wherein the PG electrode and the common lead coil are configured to provide electrical shocks for antiarrhythmic therapy.

In some aspects, the common lead coil extends along the chest of the patient from the anterior of the chest to the distal end, wherein the distal end is positioned at or beyond the midaxillary line of the patient. In certain aspects, the distal end is positioned at or beyond a posterior axillary line of the patient.

In some aspects, an active length of the common lead coil is at least 35 cm from the proximal end to the distal end.

In accordance with one or more embodiments herein, a subcutaneous implantable medical system is provided that includes a pulse generator (PG) configured to be positioned subcutaneously within a pectoral region of a chest of a patient. The PG has a housing that includes a PG electrode.

The PG has an electronics module. The subcutaneous implantable medical system also includes an elongated lead that is electrically coupled to the pulse generator. The elongated lead includes a common lead coil that extends between a proximal end and a distal end. The proximal end is configured to be positioned along an anterior of the chest of the patient, and the distal end is configured to be positioned along a posterior of the patient or a side of the patient. The common lead coil is configured to be positioned subcutaneously. At least a majority of the common lead coil is configured to be positioned at or below an apex of a heart of the patient. The electronics module is configured to provide electrical shocks for antiarrhythmic therapy using the PG electrode and the common lead coil.

In some aspects, an active length of the common lead coil is at least 35 cm from the proximal end to the distal end.

In accordance with one or more embodiments herein, a method of treating a patient is provided. The method includes sensing cardiac activity of a patient with a subcutaneous implantable medical system. The subcutaneous implantable medical system includes a pulse generator (PG) positioned subcutaneously within a pectoral region of a chest of the patient. The subcutaneous implantable medical system also includes a common lead coil that extends between a proximal end and a distal end. The common lead coil is positioned subcutaneously. At least a majority of the common lead coil is positioned at or below an apex of a heart of the patient, wherein the PG electrode and the common lead coil are configured to provide electrical shocks for antiarrhythmic therapy. The method also includes providing antiarrhythmic therapy, based on the cardiac activity, by providing electrical shocks or pulses between the common lead coil and an electrode of the PG.

DETAILED DESCRIPTION

Embodiments set forth herein include implantable medical devices (SIMDs), systems that include SIMD, and methods of using and positioning the same. In particular embodiments, the SIMD includes a subcutaneous implantable cardioverter-defibrillator (S-ICD). Embodiments include a pulse generator that is positioned within a pectoral region of a chest of a patient. The PG has a housing or canister that includes a PG electrode. Embodiments also include at least one lead having first and second electrode segments with the first electrode segment positioned along an anterior of the chest of the patient and the second electrode segment positioned along a posterior of the patient. Optionally, embodiments may include additional electrode segments, such as a third or fourth electrode segment. For example, in some embodiments, the second electrode segment may comprise two electrode sub-segments.

An electrode segment represents an electrically conductive portion of the lead that is operable to deliver energy for antiarrhythmic therapy. An electrode segment may be, for example, a coil electrode, a ring electrode, or the like. As used herein, an "electrode segment" may represent a portion of a larger electrode or may be a discrete electrode that is spaced apart from other electrode segments. In such instances, the discrete electrode segments may be attached to the same lead or different leads. In particular embodiments, electrode segments may be portions of a common (or same) lead coil. For example, a first portion of the common lead coil (or first electrode segment) may be positioned along an anterior of the chest and a second portion of the common lead coil (or second electrode segment) may be positioned along a posterior of the patient. An intermediate electrode segment of the common lead coil may extend between the first and second electrode segments. Thus, the common lead coil may extend continuously from the anterior of the chest to the posterior of the patient.

For the avoidance of doubt, a claim reciting a "first electrode segment" and a "second electrode segment" does not preclude additional electrode segments (e.g., a third electrode segment or a fourth electrode segment or so forth). Such additional electrode segments may be positioned along the anterior of the chest, a lateral region of the patient, or the posterior of the patient.

The PG electrode and the first and second electrode segments may reliably provide a sufficient amount of energy for antiarrhythmic therapy (e.g., defibrillation). Embodiments may enable pulse generators with defibrillation thresholds (DFTs) that are less than known systems. For example, the DFT in some embodiments may be at most 50 Joules. The DFT in certain embodiments may be at most 45 Joules or, more particularly, at most 40 Joules. Embodiments may also enable using pulse generators or canisters with a smaller volume than known systems. For instance, a volume of the pulse generator may be at most 40 milliliters or at most 35 milliliters.

As used herein, the term "subcutaneously," when used to describe implanting a device (e.g., pulse generator, lead body, electrode, etc.), means implanting the device beneath the skin but above layers of skeletal muscle tissue, rib bones, and costal cartilage. The device is typically positioned under the subcutaneous tissue. When the term "subcutaneous" is used to characterize the entire implantable medical system, the term means that most of the operating components of the system (e.g., the pulse generator, shocking electrodes, optional sensing electrodes, lead bodies) or each and every one of the operating components is beneath the skin, but above layers of skeletal muscle tissue, rib bones, and costal cartilage. Compared to transvenous ICD implantation, subcutaneous implantation may be less complex, less invasive, and less time-consuming. In some embodiments, however, one or more components may not be subcutaneous. For example, additional electrodes may be used that are transvenous or that contact outer cardiac tissue. In alternative embodiments, the pulse generator may be implanted submuscularly (e.g., under the serratus anterior muscle) or under the serratus anterior fascia but above muscle.

Figure 1:
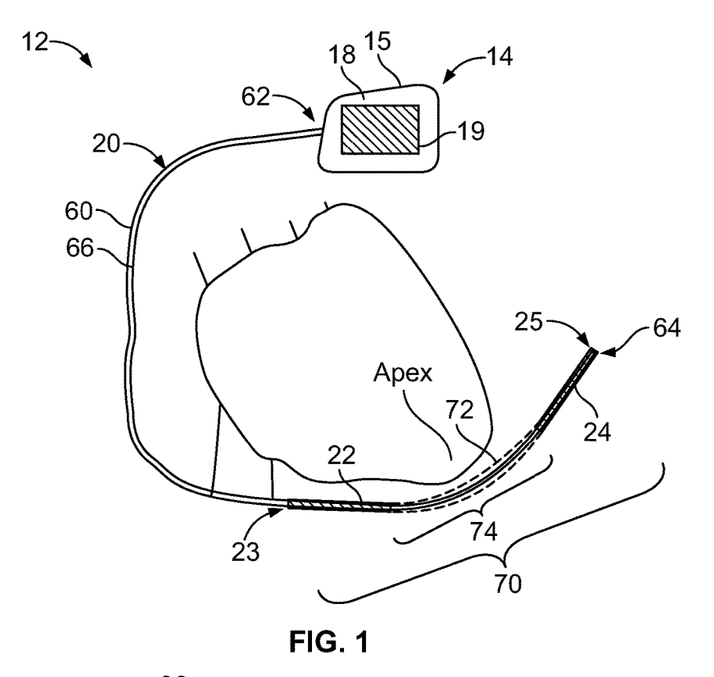
FIG. 1 illustrates a graphical representation of a heart with an implantable medical system for providing defibrillation and optionally other therapy.

FIG. 1 illustrates a graphical representation of an implantable medical system 12 that is configured to apply therapy to a heart. In particular embodiments, the system 12 may apply pacing therapy, cardiac resynchronization therapy (CRT), and general arrhythmia therapy, including defibrillation. The system 12 includes a subcutaneous implantable medical device (SIMD) 14 that is configured to be implanted in a subcutaneous area exterior to the heart. The SIMD 14 is positioned in a subcutaneous area or region.

In the illustrated embodiment, the system 12 includes only the SIMD and is entirely or fully subcutaneous. The system 12 does not require insertion of a transvenous lead. It is contemplated, however, that system 12 may include other components. For example, alternative embodiments may include a transvenous lead or a leadless electrode.

The SIMD 14 includes a pulse generator 15 and at least one lead 20 that is operably coupled to the pulse generator 15. The "at least one lead" is hereinafter referred to as "the lead." Nevertheless, it should be understood that the term, "the lead," may mean only a single lead or may mean more than one single lead. The lead 20 includes at least one electrode segment that is used for providing electrical shocks for defibrillation. Optionally, the lead 20 may include one or more sensing electrodes. The pulse generator 15 may be implanted subcutaneously and at least a portion of the lead 20 may be implanted subcutaneously. In particular embodiments, the SIMD 14 is an entirely or fully subcutaneous SIMD. In FIG. 1, the SIMD 14 is positioned within a pectoral region. Optionally, the SIMD 14 may be positioned in a different subcutaneous region. The SIMD 14 may detect or sense cardiac activity (e.g., cardiac rhythm). The SIMD 14 is configured to deliver various arrhythmia therapies, such as defibrillation therapy, pacing therapy, antitachycardia pacing therapy, cardioversion therapy, and the like, based on the cardiac activity.

The pulse generator 15 includes a housing or canister 18. The pulse generator 15 is configured to be connected to the lead 20 of the system 12. The pulse generator 15 also includes a pulse-generator (PG) electrode 19. As used herein, a pulse generator or a housing of the pulse generator "includes an electrode" when the housing forms or constitutes the electrode or when the housing (or other part of the pulse generator) has a discrete electrode attached thereto. In particular embodiments, the housing 18 forms the PG electrode 19.

The lead 20 includes an elongated lead body 60 that extends from a PG-end portion 62 to a distal tip 64. The PG-end portion 62 is operably connected to the pulse generator 15 in FIG. 1. The PG-end portion 62 may include one or more electrodes (not shown) that electrically engage respective terminals (not shown) of the pulse generator 15. More specifically, the PG-end portion 62 may be inserted into a port of the pulse generator 15 where the terminals are located.

The elongated lead body 60 includes an elongated flexible tube or sleeve 66 comprising, for example, a biocompatible material (e.g., polyurethane, silicone, etc.). The lead body 60 may include a single lumen (or passage) or multiple lumen (or passages) within the flexible tube 66. The lead 20 also includes a plurality of electrical conductors (not shown) that electrically couple the shocking electrode segments (and optionally sensing electrodes) to the pulse generator 15. The electrical conductors may be cabled conductors coated with PTFE (poly-tetrafluoroethylene) and/or ETFE (ethylenetetrafluoroethylene). The lead body 60 may be configured for receiving a stylet that enables positioning of the lead. The electrical conductors are terminated to the respective electrode segments. For example, the conductors may be terminated to respective electrodes of the PG-end portion 62 and then respective electrode segments 22, 24 (described below).

As described above, the lead 20 may include one or more electrode segments. As shown, the lead 20 includes electrode segments 22, 24 in which the electrode segments 22, 24 are spaced apart from one another having an electrical gap 74 therebetween. The lead body 60 may extend between the gap 74. The electrode segments 22, 24 may be referred to as first and second electrode segments 22, 24. The electrode segment 22 may be positioned along an anterior of the chest. The electrode segment 24 may be positioned along a lateral and/or posterior region of the patient. The electrode segments 22, 24 may be portions of the same lead, or the electrode segments may be portions of different leads. The electrode segments 22, 24 may be positioned subcutaneously at a level that aligns with the heart of the patient for providing a sufficient amount of energy for defibrillation. For example, the electrode segments 22, 24 may be positioned at or below an apex of the heart.

In some embodiments, the lead 20 includes an elongated, common lead coil 70 that includes the electrode segments 22, 24. The electrode segments 22, 24 are portions of the common lead coil 70. In FIG. 1, the common lead coil 70 extends continuously from a proximal end 23 of the electrode segment 22 to a distal end 25 of the second electrode segment 24. The distal end 25 coincides with the distal tip 64 in FIG. 1. A proximal end of an electrode segment is the end that is closest to the PG along a path of the lead. A distal end of an electrode segment is the end that is furthest from the PG along the path of the lead. The common lead coil 70 is represented by the electrode segments 22, 24 and an intermediate electrode segment 72 (indicated by dashed lines) that extends between the coils segments 22, 24. More specifically, the common lead coil 70 may be only a single coil electrode that extends continuously (e.g., without interruption) from the proximal end 23 to the distal end 25. In such embodiments, the segments may be indistinguishable.

Alternatively, the electrode segments 22, 24 may be discrete segments that are spaced apart from one another along the lead body 60 or that are positioned along different leads. For example, the electrode segment 22 may be positioned along the anterior of the chest. The lead body 60 may extend from a distal end of the electrode segment 22 to a proximal end of the electrode segment 24. As such, the gap 74 exists between the electrode segments 22, 24 along a length of the lead body 60. A length of the gap 74 may be, for example, at least 10 centimeters (cm). In certain embodiments, the length of the gap 74 may be at least 12 cm, at least 14 cm, or at least 16 cm. In particular embodiments, the length of the gap 74 may be at least 18 cm or at least 20 cm.

The electrode segments 22, 24 (or the common lead coil 70) may be positioned subcutaneously at a level that is suitable for providing a sufficient amount of energy for defibrillation. For example, the electrode segments 22, 24 (or the common lead coil 70) may be positioned subcutaneously at a level that approximately aligns with an apex of a heart of the patient. The electrode segments 22, 24 may be positioned at or below the apex of the heart. For example, the electrode segments 22, 24 (or the common lead coil 70) may be positioned along an intercostal gap between the seventh and eighth ribs of the patient or along an intercostal gap between the sixth and seventh ribs of the patient. It is contemplated, however, that the electrode segments 22, 24 (or the common lead coil 70) may be positioned at other levels with respect to the heart.

Optionally, the electrode segments 22, 24 and the PG electrode 19 (or the housing 18) may be configured to perform sensing (along one or more sensing vectors) and to deliver various types of therapy. The lead 20 is positioned such that the electrode segments 22 and 24 are positioned proximate to (but outside of) various regions or chambers of the heart. In the example of FIG. 1, the SIMD 14 is positioned above the heart, while the electrode segment 22 is positioned at a level that is approximately equal to the apex. The electrode segment 24 may be positioned along a lateral region and/or a posterior of the patient. Optionally, the housing 18 of the SIMD 14 may include one or more electrically separate electrodes, where one combination of electrodes cooperates cooperate to perform sensing and the same or a different combination of electrodes cooperates to deliver therapy.

Figure 2:
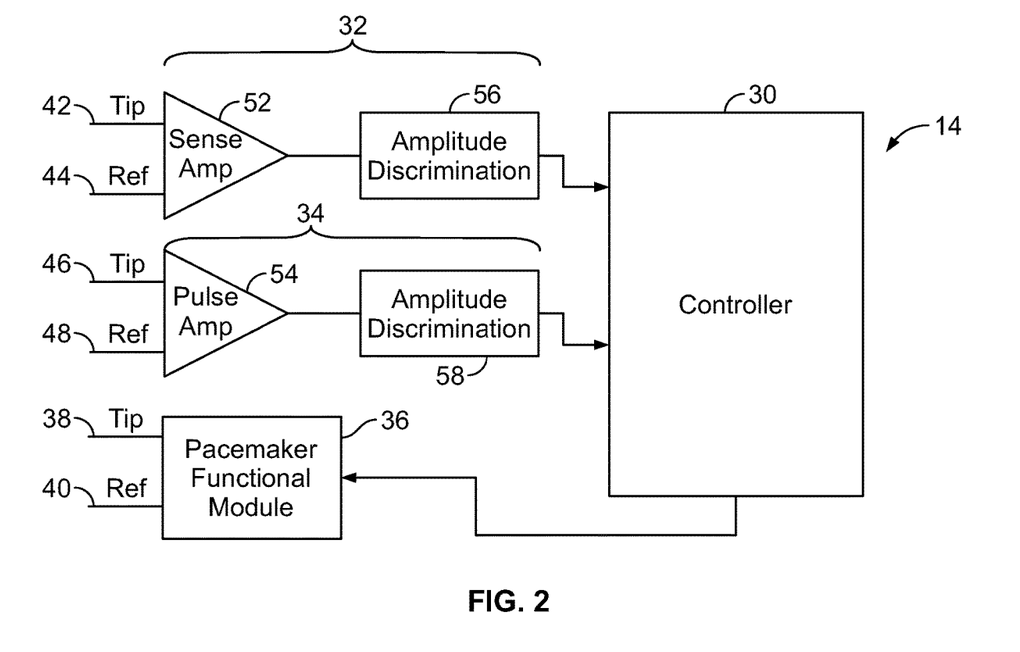
FIG. 2 illustrates a simple block diagram of at least a portion of the circuitry within a subcutaneous implantable medical device (SIMD) in accordance with an embodiment herein that may be used with the system of FIG. 1.

FIG. 2 illustrates a simple block diagram of at least a portion of the circuitry within the SIMD 14. The SIMD 14 includes a controller 30 that may be coupled to cardiac sensing circuitry 32 and pulse sensing circuitry 34. The controller 30 also utilizes or communicates with various other electronic components, firmware, software, and the like that generally perform sensing and pacing functions (as generally denoted by a pacemaker functional block 36). While the examples herein are provided for pacing and defibrillation functions, the SIMD could be programmed to perform anti-tachycardia pacing, cardiac rhythm therapy, and the like. The cardiac sensing circuitry 32 is configured to detect one or more cardiac events (e.g., ventricular fibrillation, ventricular tachycardia, or other arrhythmia). The pulse sensing circuitry 34 is configured to detect event markers.

The controller 30 is configured to analyze incoming paced cardiac events (as sensed over the cardiac sensing circuitry 32). Based on this analysis, the controller 30 in the SIMD 14 may perform various pacemaker related actions, such as setting or ending timers, recording data, delivery of therapy, and the like. The controller 30 of the SIMD 14 may also perform various cardioversion/defibrillation related functions. In the example of FIG. 2, outputs 38 and 40 represent output terminals that are coupled through a switching circuit (in the functional module 36) to corresponding electrodes on the housing of the SIMD 14. Alternatively, the outputs 38 and 40 may be coupled to respective electrode segments on along the lead 20 (FIG. 1).

Inputs 42-48 are provided to the cardiac and pulse sensing circuitry 32 and 34. By way of example, with reference to SIMD 14, inputs 42 and 44 may be coupled to sensing electrodes that supply sensed signals to a sensing amplifier 52. Inputs 46 and 48 may be coupled to the same or different sensing electrodes to provide sensed signals to a pulse amplifier 54. An output of the sensing amplifier 52 is supplied to amplitude discriminator 56, while an output of the pulse amplifier 54 is supplied to amplitude discriminator 58. Outputs of the amplitude discriminators 56 and 58 are then provided to the controller 30 for subsequent analysis and appropriate actions. The inputs 42 and 44 may be coupled to various combinations of the electrode segments 22, 24 or the PG electrode 19.

Figure 3A:
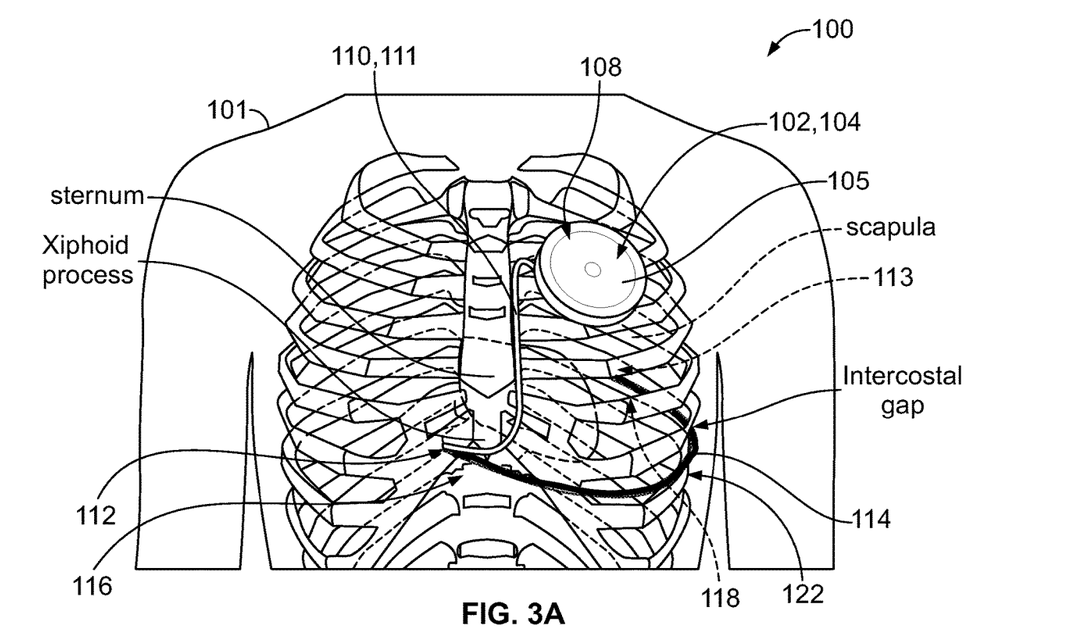
FIG. 3A illustrates an anterior view of a patient, including the relative positions of a pulse generator (PG) electrode and an elongated coil in accordance with an embodiment.
Figure 3B:
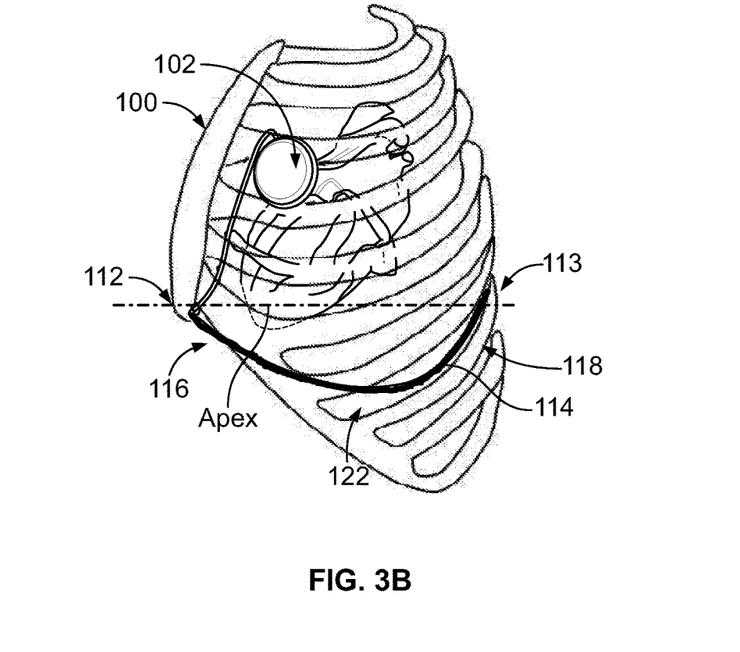
FIG. 3B is a side view of the patient illustrating the PG electrode and the elongated coil.

FIGS. 3A and 3B illustrate one configuration of an implantable medical system 100 in accordance with an embodiment. FIG. 3A illustrates the patient's torso and, particularly, the rib cage and the heart. In FIG. 3B, only the rib cage and the heart are shown. The implantable medical system 100 includes a subcutaneous implantable device (SIMD) 102 having a pulse generator 104 positioned within a pocket 108 of a pectoral region of a patient 101. The pocket 108 may be a subcutaneous pocket positioned below subcutaneous tissue but above muscle tissue. In alternative embodiments, the pocket may be submuscular (e.g., beneath the pectoral muscle).

The pulse generator 104 includes a housing and/or electrode 105 of the pulse generator 104. In the illustrated embodiment, a single lead 110 is coupled to the pulse generator 104 within the pocket 108. The lead 110 includes a lead body 111 and an elongated lead coil 114. As shown, the lead 110 extends from the pocket 108 in the pectoral region and extra-thoracically along the sternum (e.g., over the sternum or parasternally within one to three centimeters from the sternum). A proximal end 112 of the elongated lead coil 114 is located proximate to the xiphoid process. As shown, the proximal end 112 is positioned along the anterior of the chest on a right side of the sternum. Thus, in some embodiments, the lead 110 may cross over a mid-sternal line that extends through a center of the sternum.

The elongated lead coil 114 has an active length that is measured between the proximal end 112 and a distal end 113. The active length represents a length of the electrode (e.g., a coil electrode) along the lead. As shown, the elongated lead coil 114 extends from proximate to the xiphoid process, along the anterior and side of the patient within an intercostal gap, and along the posterior of the patient toward the spine. As such, the elongated lead coil 114 may wrap about the chest or torso of the patient. The distal end 113 may be positioned proximate to a scapula of the patient. For example, the distal end 113 may be positioned within the intercostal gap and proximate to the tip or the inferior angle of the scapula. The distal end 113 may be positioned between a midaxillary line and a posterior axillary line of the patient. The midaxillary line is a coronal line extending along a surface of the body passing through an apex of the axilla. The posterior axillary line is a coronal line extending parallel to the midaxillary line and through the posterior axillary skinfold. In some instances, the distal end 113 may be positioned beyond the posterior axillary line of the patient.

The elongated lead coil 114 may be characterized as having a first electrode segment 116 that includes the proximal end 112, and a second electrode segment 118 that includes the distal end 113. For embodiments in which the elongated lead coil 114 extends substantially continuously from the proximal end 112 to the distal end 113, the elongated lead coil 114 may also have an intermediate electrode segment 122 that extends between the first and second electrode segments 116, 118. The first and second electrode segments 116, 118 and the intermediate segment 122 may be indistinguishable such that the elongated coil 114 extends continuously between the proximal end 112 and the distal end 113. Alternatively, the intermediate electrode segment 122 may be discrete with respect to the first and second electrode segments 116, 118 such that gaps or spacings exist between the electrode segments.

In some embodiments, at least one of the electrode segments 116, 118, 122 is a shock coil and at least one of the electrode segments 116, 118, 122 is a sensing electrode. In other embodiments, each of the first electrode segment 116, the second electrode segment 118, and the intermediate segment 122 is a shock coil. In certain embodiments, the first electrode segment 116, the second electrode segment 118, and/or the intermediate segment 122 are electrically common (have same polarity) with one another.

As shown in FIG. 3B, the elongated lead coil 114 is positioned at or below an apex of a heart of the patient. Different portions of the lead coil 114 may have different heights or elevations relative to the heart. In certain embodiments, each of the first electrode segment 116, the second electrode segment 118, and the intermediate electrode segment 122 may be positioned at or below the apex. FIG. 3B identifies the apex and illustrates a transverse plane P that intersects the apex. In some embodiments, a small portion of the elongated coil 114 (or the first electrode segment 116) including the proximal lend 112 and/or a small portion of the elongated coil 114 (or the second electrode segment 118) including the distal end 113 may be positioned above the transverse plane P. Nonetheless, a majority of the elongated coil 114 is positioned above the apex of the heart. In particular embodiments, at least 75% of the elongated coil 114 or, more particularly, at least 85% of the elongated coil 114, more particularly, at least 95% of the elongated coil 114 is positioned at or below the apex. In certain embodiments, a majority of each of the first and second electrode segments 116 and 118 are positioned below the transverse plane P. As described herein, the elongated lead coil 114 may be positioned subcutaneously.

In FIG. 3B, the first electrode segment 116 is at or below the apex of the heart, and the second electrode segment 118 is at or below the apex of the heart. A portion of the second electrode segment 118, such as less than 50% or less than 35%, may be positioned above the plane P. In an alternative embodiment, a majority of the second electrode segment 118 may be positioned above the plane P.

In the illustrated embodiment, the elongated coil 114 extends through the same intercostal gap from the side or lateral portion of the patient to the posterior of the patient. Optionally, the elongated coil 114 may extend over a rib to move from one intercostal gap to another intercostal gap. In some cases, one or more portions of the elongated coil 114 may be positioned higher, such as even or level with a mid-plane extending through the heart.

In some embodiments, the active length of the elongated lead coil 114 is at least thirty (30) centimeters (cm). In particular embodiments, the active length of the elongated lead coil 114 may be at least thirty-five (35) cm. In more particular embodiments, the active length of the elongated lead coil 114 may be at least forty (40) cm. The active length of the elongated lead coil 114 may be at most fifty (50) cm or at most forty-five (45) cm. Accordingly, embodiments may include a lead having a single elongated coil (e.g., coil electrode) that has an active length of at least 30 cm extending from anterior to posterior of the patient while wrapping about a side (or lateral portion) of the chest.

Figure 4:
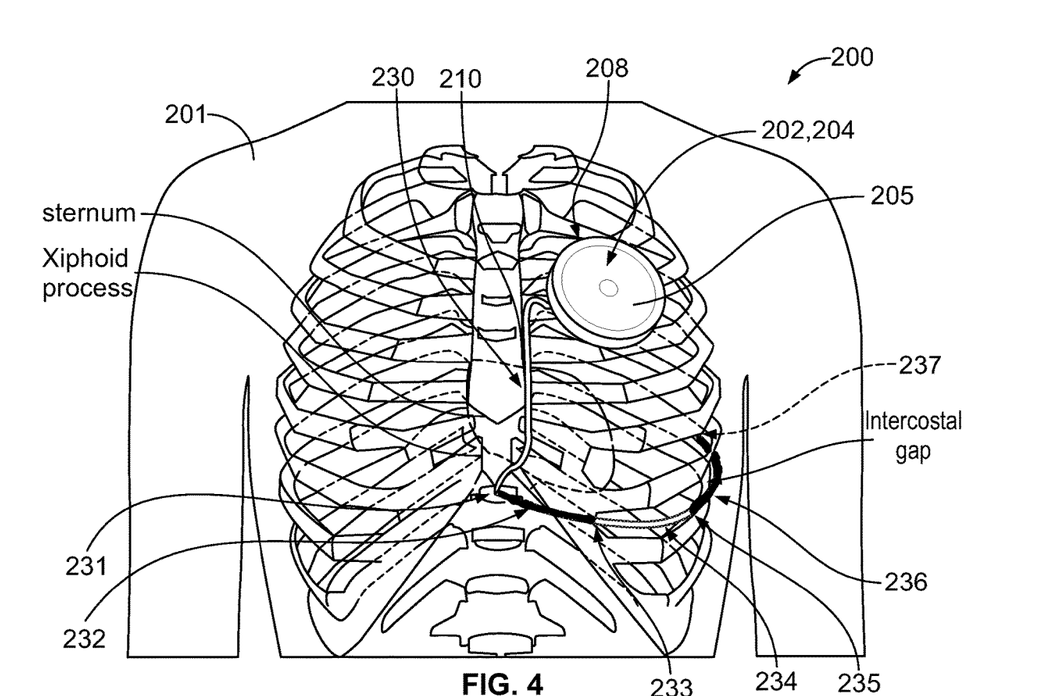
FIG. 4 illustrates relative positions of an electrode of a pulse generator (PG) and multiple coils segments positioned relative to a heart of a patient.

FIG. 4 illustrates one configuration of an implantable medical system 200 in accordance with an embodiment. The implantable medical system 200 may include features that are similar or identical to the implantable medical system 12 (FIG. 1) and/or the implantable medical system 100 (FIG. 3A). For example, the implantable medical system 200 includes a subcutaneous implantable device (SIMD) 202 having a pulse generator 204 positioned within a pocket 208 of a pectoral region of a patient 201. The pulse generator 204 includes a housing and/or electrode 205 of the pulse generator 204. In the illustrated embodiment, a lead 210 is coupled to the pulse generator 204 within the pocket 208. The lead 210 extends from the pocket 208 in the pectoral region and extra-thoracically along the sternum (e.g., over the sternum or parasternally within one to three centimeters from the sternum) toward the xiphoid process.

As shown, the lead 210 may include a series of interconnected segments. For example, the lead 210 includes a first lead segment 230, a first electrode segment 232, a second lead segment 234, and a second electrode segment 236. The first and second lead segments 230, 234 represent inactive portions of the lead 210 that do not provide electrical shock. More specifically, the first and second lead segments 230, 234 do not include electrodes that are configured to form the shock vector. The first electrode segment 232 has a proximal end 231 and a distal end 233. The second electrode segment 236 has a proximal end 235 and a distal end 237.

The first lead segment 230 extends between the pulse generator 204 and the first electrode segment 232. The first electrode segment 232 extends across the chest and is positioned subcutaneously at a level that approximately aligns with an apex of a heart of the patient. The proximal end 231 of the first electrode segment 232 is located proximate to the xiphoid process and/or a mid-sternal line. The first electrode segment 232 has an active length that extends between the proximal end 231 and the distal end 233. For example, the active length of the first electrode segment 232 in some embodiments is between 5 cm and 12 cm. In more particular embodiments, the active length of the first electrode segment 232 is between 5 cm and 8 cm.

The second lead segment 234 extends between the first electrode segment 232 and the second electrode segment 236. The second lead segment 234 forms a gap that separates the first and second electrode segments 232, 236. A length of the second lead segment 234 may be based on desired positions and active lengths of the first and second electrode segments 232, 236. Optionally, each of the first electrode segment 232, the second lead segment 234, and the second electrode segment 236 are positioned within the same intercostal gap.

The second electrode segment 236 is positioned subcutaneously at a level that approximately aligns with an apex of a heart of the patient. For example, each of the electrode segments 230, 236 may be positioned at or below the apex of the heart. As shown, the second electrode segment 236 extends from the proximal end 235, which is positioned at an anterior-lateral location of the patient, to the distal end 237, which is positioned at a posterior-lateral location. More specifically, the distal end 237 may be positioned at or beyond a midaxillary line of the patient. The second electrode segment 236 extends within an intercostal gap of the ribs and along a side of the chest or torso. The second electrode segment 236 has an active length that extends between the proximal end 235 and the distal end 237. For example, the active length of the second electrode segment 236, in some embodiments, may be at least 12 cm. In other embodiments, the second electrode segment 236 may extend further along the posterior (e.g., toward the scapula) and/or further along the anterior (e.g., begin closer to the first electrode segment 234). In some embodiments, the first electrode segment 234 and the second electrode segment 236 may be electrically common (have the same polarity).

Optionally, the first and second lead segments 230, 234 may have one or more sensing electrodes. Optionally, the first and second electrode segments 232, 236 may have one or more sensing electrodes.

During operation, the PG electrode 205 functions as a shocking electrode, and the first electrode segment 234 and the second electrode segment 236 may be electrically common (e.g., have same polarity). A shock vector is directed from the PG electrode 205 to the first electrode segment 234 and the second electrode segment 236. In some embodiments, the shock vector may be reversed. In other embodiments, the first electrode segment 234 or the second electrode segment 236 may be common with the PG electrode 205.

Figure 5:
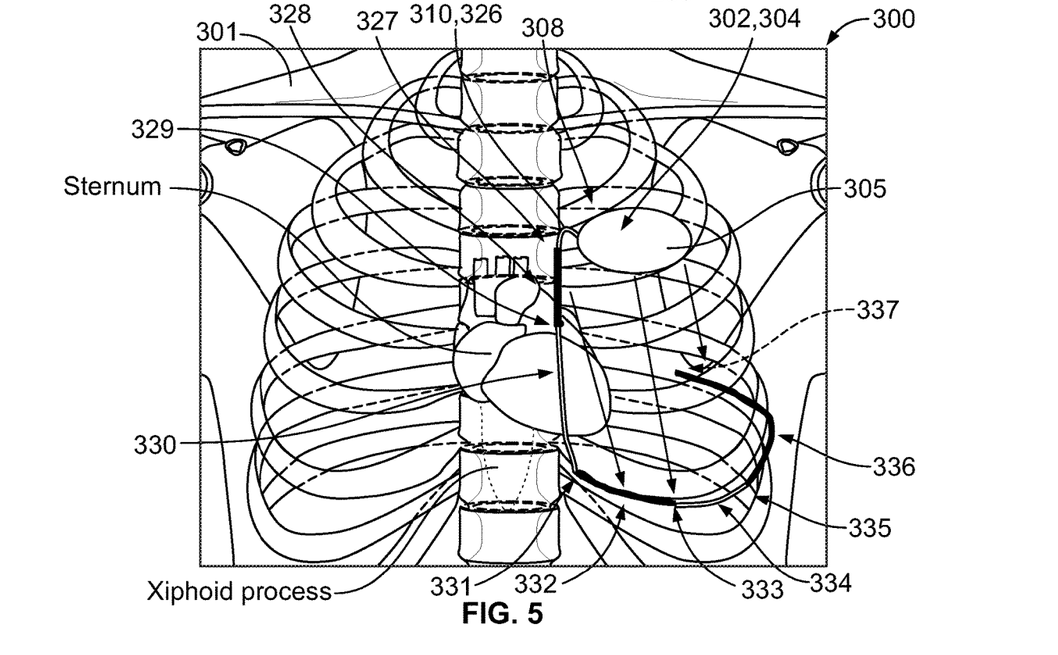
FIG. 5 illustrates relative positions of a PG electrode and multiple coils segments positioned relative to a heart of a patient, including a parasternal electrode segment.

FIG. 5 illustrates one configuration of an implantable medical system 300 in accordance with an embodiment. The implantable medical system 300 may include features that are similar or identical to the implantable medical system 12 (FIG. 1), the implantable medical system 100 (FIG. 3A), and/or the implantable medical system 200 (FIG. 4). For example, the implantable medical system 300 includes a subcutaneous implantable device (SIMD) 302 having a pulse generator 304 positioned within a pocket 308 of a pectoral region of a patient 301. The pulse generator 304 includes a housing and/or electrode 305 of the pulse generator 304. In the illustrated embodiment, a lead 310 is coupled to the pulse generator 304 within the pocket 308. The lead 310 extends from the pocket 308 in the pectoral region along the sternum of the patient 301 toward the xiphoid process.

As shown, the lead 310 may include a series of interconnected segments. For example, the lead 310 includes a parasternal lead segment 326, a parasternal electrode segment 328, a first lead segment 330, a first electrode segment 332, a second lead segment 334, and a second electrode segment 336. The parasternal lead segment 326 and the first and second lead segments 330, 334 represent non-active portions of the lead 310. The parasternal electrode segment 328 has a proximal end 327 and a distal end 329. The first electrode segment 332 has a proximal end 331 and a distal end 333. The second electrode segment 336 has a proximal end 335 and a distal end 337.

The parasternal lead segment 326 extends from the pulse generator 304 to the parasternal electrode segment 328. The parasternal electrode segment 328 is positioned subcutaneously and extends extra-thoracically along one side of the sternum (e.g., left side of patient) to the first lead segment 330. The first lead segment 330 extends from the parasternal electrode segment 328 to the first electrode segment 332. The first electrode segment 332 is positioned subcutaneously at a level that approximately aligns with an apex of a heart of the patient. The proximal end 331 of the first electrode segment 332 is located proximate to the xiphoid process and/or a mid-sternal line. The first electrode segment 332 has an active length that extends between the proximal end 331 and the distal end 333. For example, the active length in some embodiments is between 5 cm and 12 cm. In more particular embodiments, the active length is between 5 cm and 8 cm.

The second lead segment 334 extends between and joins the first electrode segment 332 and the second electrode segment 336. A length of the second lead segment 334 may be based on desired positions and active lengths of the first and second electrode segments 332, 336. As shown, each of the first electrode segment 332, the second lead segment 334, and the second electrode segment 336 are positioned within the same intercostal gap.

The second electrode segment 336 is positioned subcutaneously at a level that approximately aligns with an apex of a heart of the patient. For example, each of the electrode segments 330, 336 may be positioned at or below the apex of the heart. As shown, the second electrode segment 336 extends from the proximal end 335, which is positioned at an anterior-lateral location, to the distal end 337, which is positioned at a posterior location. More specifically, the second electrode segment 336 extends within an intercostal gap along a side or lateral portion of the chest and extends toward a tip or inferior angle of the scapula. The second electrode segment 336 has an active length that extends between the proximal end 335 and the distal end 337. For example, the active length of the second electrode segment 336, in some embodiments, may be at least 12 cm (e.g., 15 cm). In other embodiments, the second electrode segment 336 may extend further along the posterior (e.g., toward the scapula) and/or further along the anterior (e.g., begin closer to the first electrode segment 332).

During operation, the PG electrode 305 and the parasternal electrode segment 328 may function as shocking electrodes, and the first electrode segment 332 and the second electrode segment 336 may be electrically common (have the same polarity). A shock vector is indicated by the arrows in FIG. 5. Alternatively, the parasternal electrode segment 328 may be sensing electrode.

Figure 6:
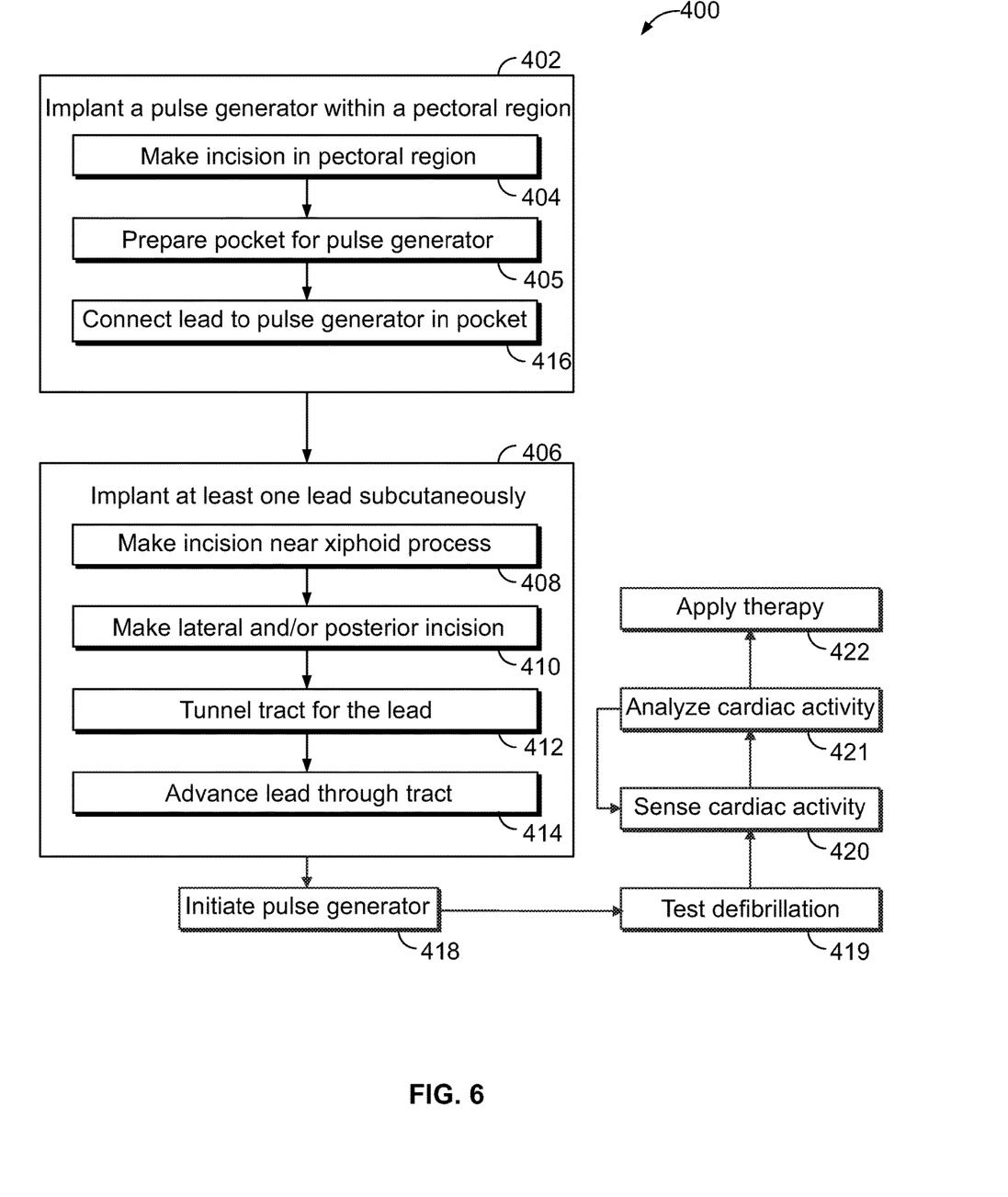
FIG. 6 illustrates a flow chart for implanting a subcutaneous medical system in accordance with an embodiment.

FIG. 6 illustrates a flow chart of a method 400 for implanting a subcutaneous implantable medical system in accordance with an embodiment. The subcutaneous implantable medical system may be similar or identical to the subcutaneous implantable medical systems described herein. The method 400 includes implanting, at 402, a pulse generator (PG) subcutaneously within a pectoral region of a chest of a patient. The PG has a housing that includes a PG electrode. For example, implanting, at 402, may include making an incision, at 404, in the chest of the patient. The incision may be performed in a pectoral region, such as a left pectoral region, and based on the anatomical location of the heart. For instance, the incision may be made approximately 2-4 cm below the clavicle, extending from the mid-clavicular region to proximate to and above the humeral-pectoral groove. The lateral extent of the incision may be based on a size of the pulse generator.

At 405, a pocket may be formed. The pocket may be subcutaneous or submuscular. The pocket may be completed before or after positioning the lead as described below. For subcutaneous pockets, the subcutaneous tissue may be dissected or separated from the pectoral fascia using a designated tool (e.g., knife). In some embodiments, an inflatable balloon may be inserted through the incision and inflated to displace the subcutaneous tissue. For submuscular pockets, the transverse muscle fibers of the pectoralis major may be separated for providing access in front of the pectoralis minor. The pulse generator may be positioned within the pocket before or after lead placement.

The method also includes implanting, at 406, at least one lead having first and second electrode segments. The implanting, at 406, may include making an access incision, at 408 and, optionally, making one or more other access incisions at 410. Access incisions may be used to manipulate the lead for placing the first and second electrode segments at designated positions. The access incision made at 408 may be proximate to the xiphoid process. The access incision(s) made at 410 may be along a side and/or posterior of the patient.

Implanting, at 406, may also include tunneling, at 412, a tract between the different incisions and advancing the lead through the tract. For example, a tunneling device (e.g., elongated tube) may be inserted through the first access incision (e.g., the xiphoid incision). The tunneling device separates the subcutaneous tissue from underlying tissue (e.g., muscle, bone) between the first access incision and the pocket. When an end of the tunneling device is accessible through the pocket, a distal end of the lead may be coupled to the end of the tunneling device (e.g., through a suture loop). The tunneling device is then withdrawn from the first access incision, thereby pulling the lead through the newly-formed tract between the pocket and the first access incision.

Subsequently, the tunneling device may be inserted through the second access incision and advanced toward the first access incision along an intercostal gap. When the end of the tunneling device is accessible through the first access incision, the lead may be coupled to the end of the tunneling device. The tunneling device is then withdrawn from the second access incision, thereby pulling the lead through the newly-formed tract between the first access incision and the second access incision. This process may be repeated as necessary for positioning the lead. Although the above describes moving the lead from the pocket to a final access incision (e.g., posterior incision), the process may be performed in reverse such that the lead is moved from the final access incision (e.g., posterior incision) toward the pocket.

After positioning the first and second electrode segments, the pulse generator may be connected to the lead at 416. More specifically, an end portion of the lead may be inserted into a port of the pulse generator. Optionally, the lead may include a parasternal electrode segment. In such embodiments, the method may include positioning the parasternal electrode segment along the sternum.

The method may also include initiating (e.g., activating) the pulse generator, at 418. For example, an external device (e.g., programmer) may be communicatively coupled to the pulse generator. The pulse generator may communicate identification data to the pulse generator (e.g., obtain model and serial number). The external device may generate a chart that correlates to the patient having the pulse generator. The external device may instruct the pulse generator to perform an electrode integrity check and measure parameters of the electrodes (e.g., impedance of shock electrode(s)). The external device and/or the pulse generator may determine a sensing configuration for the pulse generator based on cardiac activity. During initiation of the pulse generator, at 418, therapy parameters may be selected by the user.

Optionally, the pulse generator may be implemented with the hardware, firmware and other components of one or more of implantable medical devices (IMDs) that include neurostimulator devices, implantable leadless monitoring and/or therapy devices, and/or alternative implantable medical devices, although implemented as a subcutaneous implantable medical device. For example, the SIMD may represent a cardioverter, cardiac rhythm management device, defibrillator, neurostimulator, leadless monitoring device, leadless pacemaker and the like. For example, the IMD may include one or more structural and/or functional aspects of the device(s) described in U.S. Pat. No. 9,333,351 "Neurostimulation Method And System To Treat Apnea" and U.S. Pat. No. 9,044,610 "System And Methods For Providing A Distributed Virtual Stimulation Cathode For Use With An Implantable Neurostimulation System", which are hereby incorporated by reference. Additionally or alternatively, the IMD may include one or more structural and/or functional aspects of the device(s) described in U.S. Pat. No. 9,216,285 "Leadless Implantable Medical Device Having Removable And Fixed Components" and U.S. Pat. No. 8,831,747 "Leadless Neurostimulation Device And Method Including The Same", which are hereby incorporated by reference. Additionally or alternatively, the IMD may include one or more structural and/or functional aspects of the device(s) described in U.S. Pat. No. 8,391,980 "Method And System For Identifying A Potential Lead Failure In An Implantable Medical Device" and U.S. Pat. No. 9,232,485 "System And Method For Selectively Communicating With An Implantable Medical Device", which are all hereby incorporated by reference in their entireties.

At 419, a defibrillation test may be performed to determine a defibrillation threshold. The test may be administered prior to or after closing the incision. The defibrillation threshold is a quantitative estimate of the ability of the heart to defibrillate. The defibrillation threshold is typically defined as the minimum shock strength that causes defibrillation. The defibrillation threshold can be measured by changing the voltages in subsequent VF inductions in accordance with a predetermined protocol. For example, the stored voltages may be incrementally decreased for subsequent VF inductions until the first shock is unable to defibrillate. This is referred to as a step-down to failure test. If a high defibrillation threshold is identified, it may be desirable to make adjustments to the system. For example, the leads could be repositioned, the leads could be switched-out, portions of the electrodes could be capped, or another lead may be added. The defibrillation testing may be performed using an external device (e.g., programmer) that is communicatively coupled to the pulse generator.

Another defibrillation test may including applying the same energy twice. The first electrical shock may be programmed to deliver an amplitude that is less than 10 Joules from the maximum capacity of the system. To verify the effectiveness of the shock, the same amplitude may then be applied a second time. At least three to five minutes may separate subsequent applications to allow hemodynamic recovery and to minimize the cumulative effect of the electrical shocks. If the electrical shock delivered by the implantable defibrillator is ineffective, a rescue shock can be delivered either by an external defibrillator or through the implanted defibrillator.

After closing the incisions, the method may also include sensing cardiac activity at 420 and analyzing, at 421, the cardiac activity to determine whether a cardiac event-of-interest has occurred. In response to determining that a cardiac event-of-interest has occurred, a therapy may be applied, at 422. For example, the pulse generator may sense subcutaneous signals (e.g., subcutaneous ECG signals) and a cardiac rhythm using a combination of the electrodes. The pulse generator may process the cardiac signals (e.g., filter and/or amplify) and analyze the cardiac activity to determine whether an event that requires therapy is occurring. If the pulse generator determines that a cardiac event-of-interest is occurring, such as ventricular fibrillation, ventricular tachycardia, or other arrhythmia, the pulse generator may apply therapy (e.g., electrical shock) to the heart using a combination of the electrodes.

Figure 7:
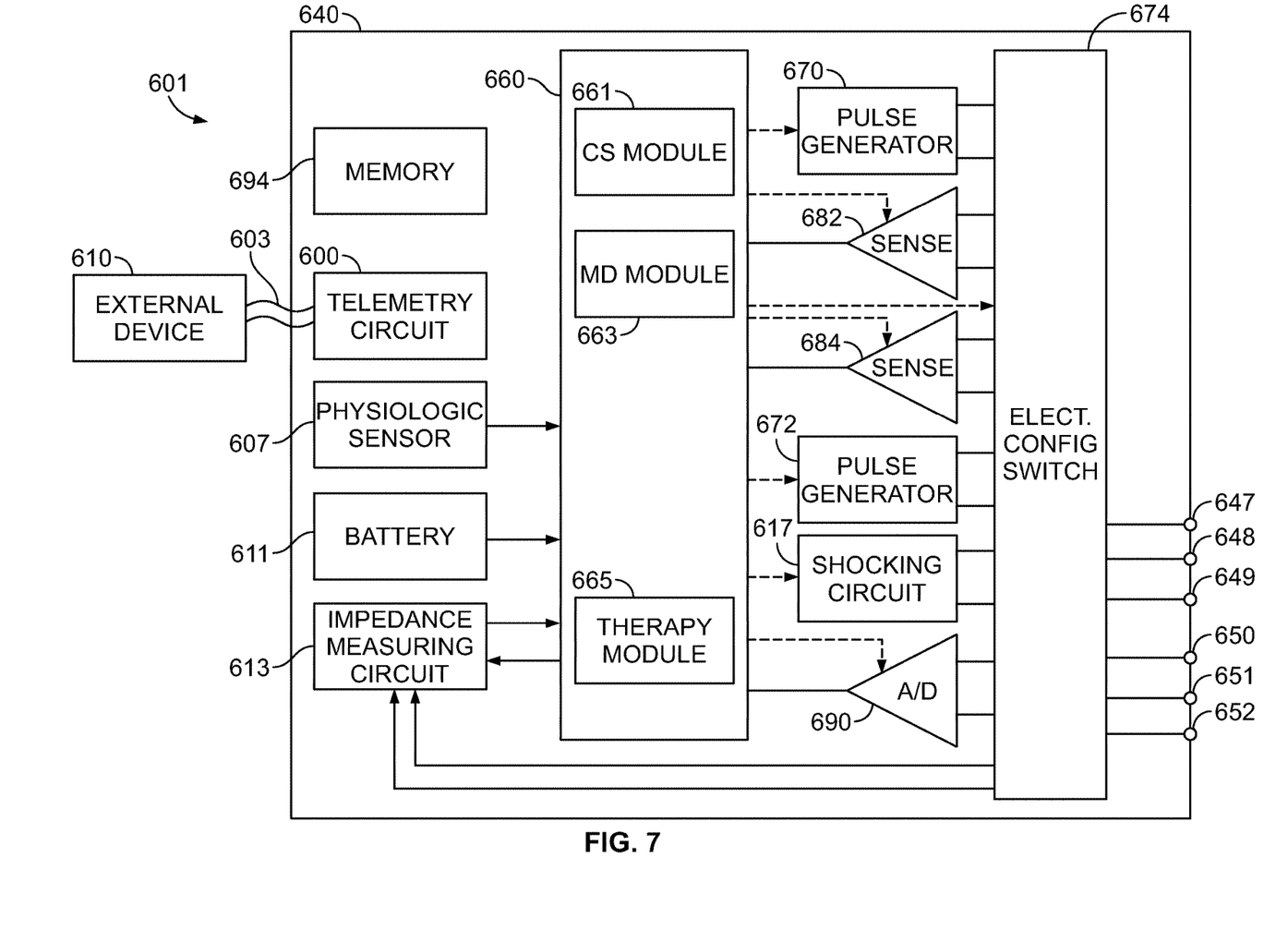
FIG. 7 illustrates a block diagram of an SIMD in accordance with an embodiment that is capable of performing stimulation therapy, including cardioversion, defibrillation, and pacing stimulation.

FIG. 7 illustrates a block diagram of an SIMD. The SIMD is capable of performing stimulation therapy, including cardioversion, defibrillation, and pacing stimulation. The SIMD is hereinafter referred to as the device 601. While a particular multi-element device is shown, this is for illustration purposes only. It is understood that the appropriate circuitry could be duplicated, eliminated or disabled in any desired combination to provide a device capable of monitoring impedance and/or cardiac signals, and/or treating the appropriate chamber(s) with cardioversion, defibrillation and pacing stimulation.

The housing 640 for the device 601 is often referred to as the "canister," "can," "case," or "case electrode" and may be programmably selected to act as the shock electrode and/or as a return electrode for some or all sensing modes. The housing 640 may further be used as a return electrode alone or in combination with one or more other electrodes. The housing 640 further includes a connector (not shown) having a plurality of terminals 647-652. To achieve sensing, pacing, and shocking in connection with desired chambers of the heart, the terminals 647-652 are selectively connected to corresponding combinations of electrodes.

The device 601 includes a programmable microcontroller 660 that controls the various modes of sensing and stimulation therapy. The microcontroller 660 includes a microprocessor, or equivalent control circuitry, designed specifically for controlling sensing impedance derivation and the delivery of stimulation therapy and may further include RAM or ROM memory, logic and timing circuitry, state machine circuitry, and I/O circuitry. The microcontroller 660 includes the ability to process or monitor input signals (data) as controlled by a program code stored in memory. The details of the design and operation of the microcontroller 660 are not critical to the present invention. Rather, any suitable microcontroller 660 may be used.

The microcontroller 660 includes inputs that are configured to collect cardiac signals associated with electrical or mechanical behavior of a heart over at least one cardiac cycle. The cardiac signals may be from the cardiac sensing circuit 682 and representative of electrical behavior of the heart. The circuit 682 may provide separate, combined, composite or difference signals to the microcontroller 660 representative of the sensed signals from the electrodes. Optionally, the cardiac signals may be the output of the A/D circuit 690 that are representative of electrical behavior of the heart. The cardiac signals may be the output of the physiologic sensor 607 that are representative of mechanical behavior.

The microcontroller 660 includes a cardiac signal (CS) module 661, a marker detection (MD) module 663 and a therapy module 665 (among other things). The CS module 661 is configured to analyze cardiac signals. The MD module 663 is configured to analyze signals sensed over the marker sensing channel and identify incoming event markers. The therapy module 665 is configured to modulate, over multiple cardiac cycles; at least one therapy parameter while the device 601 obtains a collection of at least one CSF indicators associated with different therapy parameters. The therapy module 665 is further configured to adjust a therapy configuration based on, among other things, the cardiac signals and based on the event markers.

The microcontroller 660 further controls a shocking circuit 617 by way of a control signal. The shocking circuit 617 generates stimulating pulses of low (up to 0.5 Joules), moderate (0.5-10 Joules), or high energy (11 to 50 Joules), as controlled by the microcontroller 660. Stimulating pulses may be applied to the patient's heart through at least two shocking electrodes.

One or more pulse generators 670 and 672 generate various types of therapy, such as pacing and ATP stimulation pulses for delivery by desired electrodes. The electrode configuration switch 674 (also referred to as a switch bank) controls which terminals 647-652 are connected to the pulse generators 670, 672, thereby controlling which electrodes receive a therapy. The pulse generators, 670 and 672, may include dedicated, independent pulse generators, multiplexed pulse generators, shared pulse generators or a single common pulse generator. The pulse generators 670 and 672 are controlled by the microcontroller 660 via appropriate control signals to trigger or inhibit stimulation pulses. The microcontroller 660 further includes timing control circuitry which is used to control the timing of such stimulation pulses (e.g., pacing rate, atrio-ventricular (AV) delay, atrial interconduction (A-A) delay, or ventricular interconduction (V-V) delay, etc.) as well as to keep track of the timing of refractory periods, PVARP intervals, noise detection windows, evoked response windows, alert intervals, marker channel timing, etc.

An electrode configuration switch 674 connects the sensing electronics to the desired terminals 647-652 of corresponding sensing electrodes. For example, a portion of the terminals may be coupled to electrodes configured to define a sensing and/or shocking vector that passes through the left ventricle. The electrode configuration switch 674 may connect terminals to the event marker sensing circuit 684 (which corresponds to the event marker sensing channel) and the microcontroller. The circuit 684 may amplify, filter, digitize and/or otherwise process the sensed signals from the select electrodes.

The electrode configuration switch 674 also connects various combinations of the electrodes to an impedance measuring circuit 613. The impedance measuring circuit 613 includes inputs to collect multiple measured impedances between corresponding multiple combinations of electrodes. For example, the impedance measuring circuit 613 may collect a measured impedance for each or a subset of the active sensing vectors. Optionally, the impedance measuring circuit 613 may measure respiration or minute ventilation; measure thoracic impedance for determining shock thresholds; detect when the device has been implanted; measure stroke volume; and detect the opening of heart valves, etc.

The electrode configuration switch 674 includes a plurality of switches for connecting the desired electrodes to the appropriate I/O circuits, thereby providing complete electrode programmability. The electrode configuration switch 674, in response to a control signal from the microcontroller 660, determines the polarity of the stimulation pulses (e.g., unipolar, bipolar, co-bipolar, etc.) by selectively closing the appropriate combination of switches (not specifically shown). The outputs of the cardiac sensing and event marker sensing circuits 682 and 684 are connected to the microcontroller 660 which, in turn, is able to trigger or inhibit the pulse generators 670 and 672, respectively. The sensing circuits 682 and 684, in turn, receive control signals from the microcontroller 660 for purposes of controlling the gain, threshold, the polarization charge removal circuitry (not shown), and the timing of any blocking circuitry (not shown).

Cardiac signals are also applied to the inputs of an analog-to-digital (ND) data acquisition system 690. The data acquisition system 690 is configured to acquire cardiac signals, convert the raw analog data into a digital signal, and store the digital signals for later processing and/or telemetric transmission to an external device 610 (e.g., programmer). The data acquisition system 690 samples cardiac signals across any pair of desired electrodes. The data acquisition system 690 may be coupled to the microcontroller 660, or other detection circuitry, for detecting an evoked response from the heart in response to an applied stimulus, thereby aiding in the detection of "capture." Capture occurs when an electrical stimulus applied to the heart is of sufficient energy to depolarize the cardiac tissue, thereby causing the heart muscle to contract.

The microcontroller 660 is further coupled to a memory 694 by a suitable data/address bus 696. The memory 694 stores programmable operating, impedance measurements, impedance derivation and therapy-related parameters used by the microcontroller 660. The operating and therapy-related parameters define, for example, pacing pulse amplitude, pulse duration, electrode polarity, rate, sensitivity, automatic features, arrhythmia detection criteria, and the amplitude, wave shape and vector of each stimulating pulse to be delivered to the patient's heart within each respective tier of therapy.

The operating and therapy-related parameters may be non-invasively programmed into the memory 694 through a telemetry circuit 600 in telemetric communication with the external device 610, such as a programmer, trans-telephonic transceiver, or a diagnostic system analyzer. The telemetry circuit 600 is activated by the microcontroller 660 by a control signal. The telemetry circuit 600 advantageously allows data and status information relating to the operation of the device (as contained in the microcontroller 660 or memory 694) to be sent to an external device through an established communication link 603.

The device 601 may include a physiologic sensor 607 to adjust pacing stimulation rate according to the exercise state of the patient. The physiological sensor 607 may further be used to detect changes in cardiac output, changes in the physiological condition of the heart, or diurnal changes in activity (e.g., detecting sleep and wake states). The battery 611 provides operating power to all of the circuits shown in FIG. 7.

It will be readily understood that the components of the embodiments as generally described and illustrated in the Figures herein, may be arranged and designed in a wide variety of different configurations in addition to the described example embodiments. Thus, the following more detailed description of the example embodiments, as represented in the Figures, is not intended to limit the scope of the embodiments, as claimed, but is merely representative of example embodiments.

Reference throughout this specification to "one embodiment" or "an embodiment" (or the like) means that a particular feature, structure, or characteristic described in connection with the embodiment is included in at least one embodiment. Thus, appearances of the phrases "in one embodiment" or "in an embodiment" or the like in various places throughout this specification are not necessarily all referring to the same embodiment.

Furthermore, the described features, structures, or characteristics may be combined in any suitable manner in one or more embodiments. In the following description, numerous specific details are provided to give a thorough understanding of embodiments. One skilled in the relevant art will recognize, however, that the various embodiments can be practiced without one or more of the specific details, or with other methods, components, materials, etc. In other instances, well-known structures, materials, or operations are not shown or described in detail to avoid obfuscation. The following description is intended only by way of example, and simply illustrates certain example embodiments.

It is to be understood that the above description is intended to be illustrative, and not restrictive. For example, the above-described embodiments (and/or aspects thereof) may be used in combination with each other. In addition, many modifications may be made to adapt a particular situation or material to the teachings of the inventive subject matter without departing from its scope. While the dimensions and types of materials described herein are intended to define the parameters of the inventive subject matter, they are by no means limiting and are exemplary embodiments. Many other embodiments will be apparent to one of ordinary skill in the art upon reviewing the above description. The scope of the inventive subject matter should, therefore, be determined with reference to the appended claims, along with the full scope of equivalents to which such claims are entitled. In the appended claims, the terms "including" and "in which" are used as the plain-English equivalents of the respective terms "comprising" and "wherein." Moreover, in the following claims, the terms "first," "second," and "third," etc. are used merely as labels, and are not intended to impose numerical requirements on their objects. Further, the limitations of the following claims are not written in means-plus-function format and are not intended to be interpreted based on 35 U.S.C. § 112(f) unless and until such claim limitations expressly use the phrase "means for" followed by a statement of function void of further structure.

What is claimed is:

1. A method comprising:
    forming a pocket within a pectoral region of a chest of a patient, the pocket shaped to receive a pulse generator (PG), the PG having a housing that includes a PG electrode;
    making a first access incision proximate to a xiphoid process;
    inserting a tunneling device through the first access incision to form a first tract extending between the first access incision and the pocket;
    pulling a lead through the first tract between the pocket and the first access incision, the lead having first and second electrode segments;
    making a second access incision positioned at or beyond a mid-auxiliary line;
    inserting the tunneling device through the second access incision to form a second tract along an intercostal gap between the second access incision and the first access incision;
    pulling the lead through the second tract between the first access incision and the second access incision such that the first and second electrode segments are positioned subcutaneously at or below an apex of a heart of the patient; and
    connecting the lead to the PG, wherein the PG electrode and the first and second electrode segments are configured to provide electrical shocks for antiarrhythmic therapy.

2. The method of claim 1, wherein the pulling the lead through the first tract includes pulling the lead in a direction extending from the pocket to the first access incision and wherein the pulling the lead through the second tract includes pulling the lead in a direction extending from the first access incision to the second access incision, the lead being pulled through the first tract before being pulled through the second tract.

3. The method of claim 1, wherein the pulling the lead through the second tract includes pulling the lead in a direction extending from the second access incision to the first access incision, and wherein the pulling the lead through the first tract includes pulling the lead in a direction extending from the first access incision to the pocket, the lead being pulled through the second tract before being pulled through the first tract.

4. The method of claim 1, wherein the pulling the lead through the first track further comprises coupling the tunneling device to the lead and withdrawing the tunneling device from the first tract to pull the lead through the first tract, and wherein the pulling the lead through the second track further comprises coupling the tunneling device to the lead and withdrawing the tunneling device from the second tract to pull the lead through the second tract.

5. The method of claim 1, wherein the pulling the lead through the second tract positions the lead such that the first and second electrode segments are positioned subcutaneously at or below an apex of the heart of the patient.

6. The method of claim 1, wherein the first and second access incisions and the second tract are positioned relative to a transverse plane that intersects the apex of the heart such that a portion of at least one of the first or second electrode segments is positioned at or above the transverse plane.

7. The method of claim 6, wherein the first and second access incisions and the second tract are positioned relative to the transverse plane such that at least 75% of the portion is at or above the apex of the heart.

8. The method of claim 6, wherein the first and second access incisions and the second tract are positioned relative to the transverse plane such that at least 85% of the portion is at or above the apex of the heart.

9. The method of claim 6, wherein the first and second access incisions and the second tract are positioned relative to the transverse plane such that a majority of each of the first or second electrode segments is below the transverse plane corresponding to the apex of the heart.

10. The method of claim 1, further comprising implanting the PG in the pocket after the lead is connected to the PG.

11. The method of claim 1, wherein the first tract is located proximate to the sternum.

12. The method of claim 1, wherein the first and second electrode segments are portions of a common lead coil that extends from a proximal end of the first electrode segment to a distal end of the second electrode segment, the common lead coil extending along the chest of the patient from an anterior of the chest toward a side of the patient, wherein the second electrode segment extends to or beyond a midaxillary line of the patient.

13. The method of claim 1, wherein an active length of the common lead coil is at least 35 cm from the proximal end of the first electrode segment to the distal end of the second electrode segment.

14. The method of claim 1, wherein the first and second electrode segments are spaced apart from one another, the second electrode segment being longer than the first electrode segment.

15. The method of claim 14, wherein the second electrode segment has an active length measured between proximal and distal ends of the second electrode segment, the active length being at least 12 centimeters (cm), wherein the second electrode segment extends beyond a posterior axillary line.

16. The method of claim 1, wherein the lead is positioned such that the lead extends away from the pulse generator, extra-thoracically along a sternum, and along an intercostal gap so that a distal end of the lead is positioned at or beyond a midaxillary line of the patient.

17. The method of claim 1, wherein a defibrillation threshold (DFT) is at most 50 Joules and a volume of the pulse generator is at most 40 milliliters.

18. A method comprising:
forming a pocket within a pectoral region of a chest of a patient, the pocket shaped to receive a pulse generator (PG), the PG having a housing that includes a PG electrode, the pulse generator having a volume that is at most 40 milliliters;
making a first access incision proximate to a xiphoid process;
inserting a tunneling device through the first access incision to form a first tract extending between the first access incision and the pocket;
pulling a lead through the first tract between the pocket and the first access incision, the lead having first and second electrode segments;
making a second access incision positioned at or beyond a mid-auxiliary line;
inserting the tunneling device through the second access incision to form a second tract along an intercostal gap between the second access incision and the first access incision;
pulling the lead through the second tract between the first access incision and the second access incision such that the first and second electrode segments are positioned subcutaneously at or below an apex of a heart of the patient, wherein the PG electrode and the first and second electrode segments define a shocking vector that exhibits a defibrillation threshold (DFT) that is at most 50 Joules; and
connecting the lead to the PG, wherein the PG electrode and the first and second electrode segments are configured to provide electrical shocks for antiarrhythmic therapy.

19. The method of claim 18, wherein the first and second electrode segments are portions of a common lead coil that extends from a proximal end of the first electrode segment to a distal end of the second electrode segment, the common lead coil having an active length that is at least 35 cm from the proximal end of the first electrode segment to the distal end of the second electrode segment, the common lead coil extending along the chest of the patient from the anterior of the chest toward the side of the patient and extending to or beyond a midaxillary line of the patient, the pulse generator operable to generate a defibrillating energy of at most 50 Joules.

20. The method of claim 18, wherein the pulling the lead through the first tract includes pulling the lead in a direction extending from the pocket to the first access incision and wherein the pulling the lead through the second tract includes pulling the lead in a direction extending from the first access incision to the second access incision, the lead being pulled through the first tract before being pulled through the second tract, wherein the first and second access incisions and the formation of the second tract are positioned relative to a transverse plane that intersects the apex of the heart such that a portion of at least one of the first or second electrode segments is positioned with at least 75% of at least one of the first or second electrode segments at or above the apex of the heart.

* * * * *